United States Patent [19]
Burns

[11] Patent Number: 5,297,960
[45] Date of Patent: Mar. 29, 1994

[54] EXPANDABLE DUAL DENTAL IMPRESSION TRAY

[76] Inventor: William F. Burns, 21 Brooklawn Dr. Box 262, Pompton Plains, N.J. 07444

[21] Appl. No.: 980,346

[22] Filed: Nov. 23, 1992

[51] Int. Cl.⁵ ............................................. A61C 9/00
[52] U.S. Cl. ......................................... 433/41; 433/42
[58] Field of Search .................................... 433/41, 42

[56] References Cited

U.S. PATENT DOCUMENTS

| | | | |
|---|---|---|---|
| 2,703,452 | 3/1955 | Getz | 433/38 |
| 3,890,711 | 6/1975 | Burns | 433/41 |
| 4,145,812 | 3/1979 | Johnson et al. | 433/41 |
| 4,449,927 | 5/1984 | Taylor et al. | 433/38 |

Primary Examiner—John J. Wilson
Attorney, Agent, or Firm—Martin J. Spellman, Jr.

[57] ABSTRACT

An adjustable dual dental impression tray for taking full mouth impressions, and in one form for quadrant impressions of upper and lower teeth simultaneously is disclosed. The tray has an interior section with spaced apart vertical walls adjoined by a mesh cloth extending horizontally between the walls. The walls of the interior section extend rearwardly. Anterior extension sections which comprise spaced apart vertical inner and outer walls which are joined by a mesh cloth extending between the inner surfaces of the walls which are joined at their anterior ends by a flexible connector. The mesh extends between the walls at approximately mid height and the interior section has horizontal slots extending through the walls and forwardly from the rear ends of the walls below the mesh at the mesh of the extensions to move forward to overlap the mesh of the anterior section. This permits the simultaneous taking of dental impressions of the upper and lower teeth.

6 Claims, 6 Drawing Sheets

EXPANDABLE DUAL DENTAL IMPRESSION TRAY

BACKGROUND OF THE INVENTION

1. Field of the Invention

The invention is concerned with dental impression trays which may be extended or contracted to adjust for the specific size and configuration of individual patient's mouths and in preferred forms may be used to take impressions of the upper and lower arches simultaneously.

2. Prior Art

A current type of impression tray that is widely used consists of a pair of spaced apart vertical plastic walls joined by a horizontal mesh and having a gripping area at the anterior end and most often a posterior strap or loop joining the walls at the posterior ends of the walls. The dentist must stock a large number of different sizes to accommodate the vagaries of different patient mouths. The present tray in contrast is easily adapted to variations in the dental arch.

U.S. Pat. No. 4,145,812—Johnson discloses an adjustable dental impression tray in which an extension piece telescopes over secondary leg portions of the primary unit. Flap and tab combinations hold the adjusted extension in a selected position.

U.S. Pat. No. 4,368,040—Weissman shows a complex tray with grooved sides for holding an elongated strap.

U.S. Pat. No. 2,529,429—Spiro discloses a two-part tray held together with a hinge. The relative movement of the two parts is up and down and the purpose is to place additional pressure on the impression taking compound.

U.S. Pat. No. 3,890,711 of the present applicant concerns an adjustable dental impression tray including a primary unit and a slidable unit mounted telescopically on the primary unit with a T shaped slot and elongated slot and securing means including a mounting head and threaded stem going through both slots and a retainer head on the projecting end of the stem to hold the securing means together. This tray is useful, however, the securing means is somewhat complex in construction and requires intense concentration to use. Further, the invention therein is not readily adaptable to use with the plastic wall and mesh devices currently in wide use.

Of background interest are the following references relating to early developments in adjustable dental trays. U.S. Pat. Nos. 753,679 of Mar. 1, 1904; 755,670 of Mar. 29, 1904; 765,919 of Jul. 26, 1904; 1,054,999 of Mar. 4, 1913; 1,493,417 of May 6, 1924; 2,426,388 of Aug. 26, 1947; Swiss Pat. No. 57,395 of Jul. 21, 1911 and German Pat. No. 1,083,017 of Jun. 9, 1960.

None of these devices disclosed provide the simplicity of construction, the control and locking of the relatively adjustable parts, and resulting ease of use of my invention for taking dual dental impressions simultaneously.

SUMMARY OF THE INVENTION

The present invention is concerned with a dual dental impression tray that is also adjustable to different sizes of patients' mouths.

The dual impression tray of the present invention enables the dentist to take impressions of both the upper and lower teeth simultaneously. The tray of this invention may be adjusted to the specific size of the patient's mouth thus eliminating the need for the dentist to stock many different sizes of trays to accommodate different mouth configurations. The use of the tray of this invention also reduces the number of steps and the time required to obtain a complete mouth impression.

In accordance with this invention, the adjustable dual impression tray comprises an anterior end portion and a moveable posterior portion(s) adjustably secured to the posterior end(s) of the anterior portion. The tray has a handle extending forwardly from the anterior end to facilitate handling of the device.

Extending rearwardly from the handle and following the curvature of a patient's gums, the anterior portion of the tray includes spaced apart inner and outer walls of sufficient height for retaining impression material for both the upper and lower teeth. Extending between the inner surfaces of the walls intermediate the height of the walls is a thin plastic mesh cloth on which the impression material is placed for both upper and lower in the usual manner.

The posterior extension portion comprises a pair of spaced apart vertical walls also having a mesh cloth extending between them at mid height and joined at their posterior ends by a connecting arm.

The walls of the posterior members are spaced apart such a distance that their interior surfaces slide along outside the exterior surfaces of the walls of the anterior part when placed in overlapping relationship.

The walls of the anterior member have horizontal slots opening at their posterior ends just above or below the level of the mesh cloth and are of a length approximately that of the posterior member. The slots are aligned with the mesh cloth of the posterior part to allow the mesh of the posterior part to slide over or under the mesh of the anterior part in overlapping relationship as the parts are moved towards or away from each other.

The exterior surfaces of the walls of the anterior member are provided with longitudinal rails of T shaped cross section towards their posterior ends which coact in sliding relationship with corresponding longitudinal recesses of T-shaped crossection in the interior surfaces of the walls of the posterior portion of the device to hold the anterior and posterior members together.

In alternative embodiments, the rails may be replaced with a longitudinal line of nibs which coact with corresponding recesses on the outside surface of the walls of the anterior portion. The arm joining the walls of the posterior member together is flexible enough to permit the walls to spread apart slightly to slide longitudinally with respect to the walls of the anterior member and then lock in the desired selected position.

Other alternative embodiments include quadrant trays and versions for upper or lower impressions only.

The trays may be molded of polyethylene, polytetrafluorethyle or other suitable plastic and the mesh embedded in the plastic in a known manner between upper and lower halves or adhesively secured.

The anterior and posterior members are assembled in sliding overlapping relation and the relative positions adjusted to fit the individual patient's mouth. The dentist then places the impression material over and/or under the mesh material and obtains the impression in the usual manner except that both upper and lower may be accomplished simultaneously as opposed to prior adjustable trays which generally allowed only an upper or lower impression to be taken at one time.

The adjustable dual impression tray of the present invention saves the dentist the necessity of stocking excessive different size trays, cuts down on the time necessary to obtain a full set of impressions, increases the accuracy of the impressions, cuts down on chair time and makes the procedure less onerous for the patient.

BRIEF DESCRIPTION OF THE DRAWING

In the accompanying drawing which forms a part of the specification.

DESCRIPTION OF ILLUSTRATIVE EMBODIMENT

Figure 1:
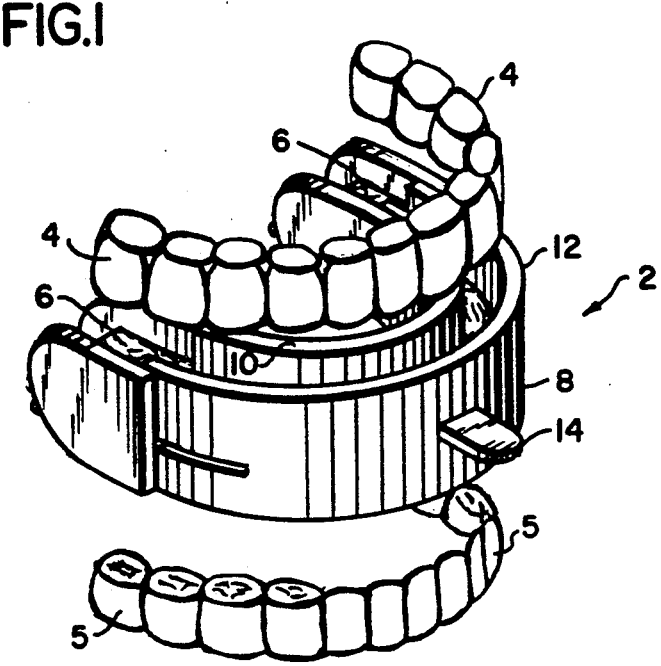
FIG. 1 is a perspective view of an anterior impression tray according to the present invention showing the tray with impression material and the upper teeth of a patient before contact with the impression material.
Figure 2:
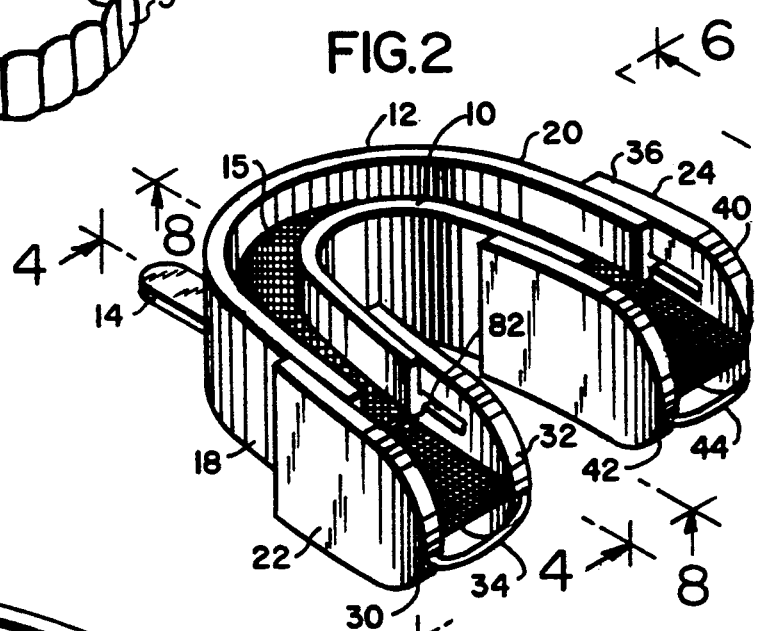
FIG. 2 is another perspective view from the rear left of the anterior impression tray of FIGS. 1, with the adjustable parts separated.

Referring to the accompanying drawing, an anterior impression tray according to the present invention is indicated in general at 2 in FIGS. 1 and 2. In FIG. 1, a patient's upper teeth 4 and lower teeth 5 are shown prior to pressing them into the impression material 6 in the tray 2. The tray 2 includes a main arcuate portion 8 with parallel spaced apart vertical walls 10 and 12. The outer wall 12 has a handle 14 at the forward end 16 to facilitate handling by the dentist.

The arcuate portion 8 extends to rearward to branches 18 and 20 which are in sliding frictional engagement extension portions 22 and 24.

Extension 22 has spaced apart vertical outer wall 26 and inner wall 28 joined at their posterior ends 30 and 32 respectively by the transverse member 34 which holds the walls 26 and 28 spaced apart and generally parallel to each other.

Similarly, extension 24 has spaced apart vertical outer wall 36 and inner wall 38 which are joined at their posterior ends 40 and 42 respectively by the transverse member 44.

Figure 3:
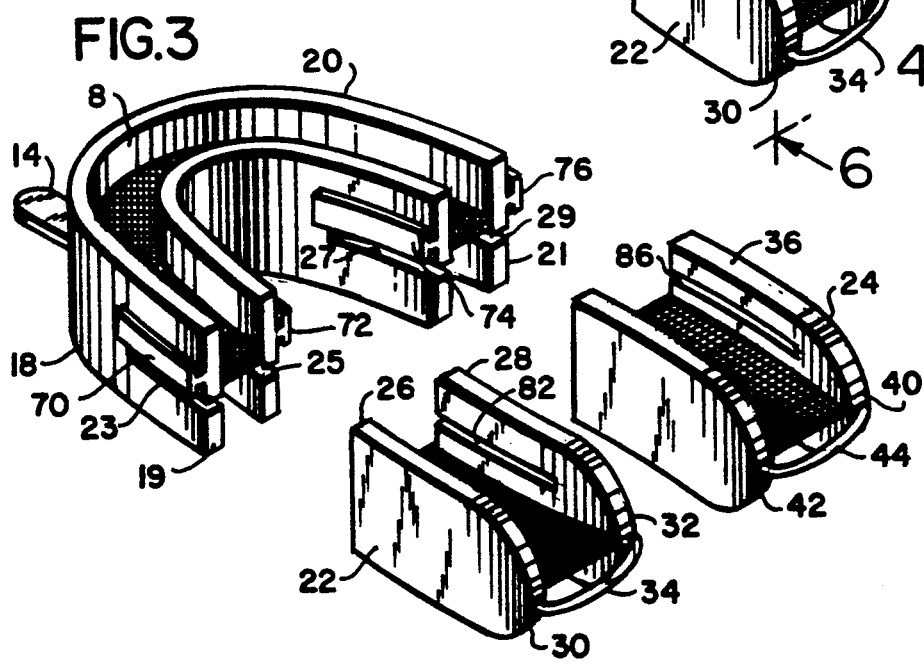
FIG. 3 is a perspective view of the anterior impression similar to FIG. 2 with the adjustable parts separated.
Figure 4A:
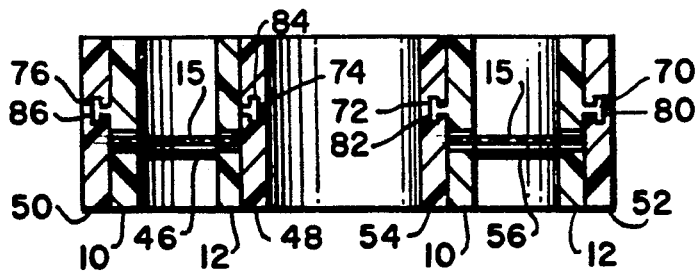
FIG. 4A is a sectional view along lines 4A—4A of FIG. 8.
Figure 4:
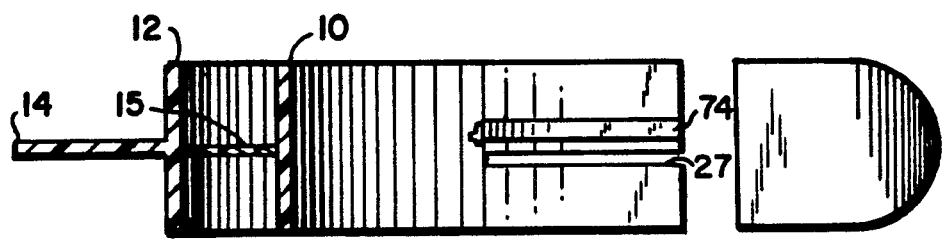
FIG. 4 is a sectional view along lines 4—4 of FIG. 2.
Figure 5:
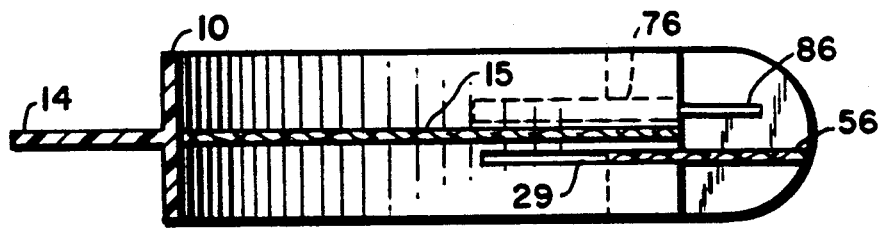
FIG. 5 is a sectional view along lines 5—5 of FIG. 7.
Figure 6:
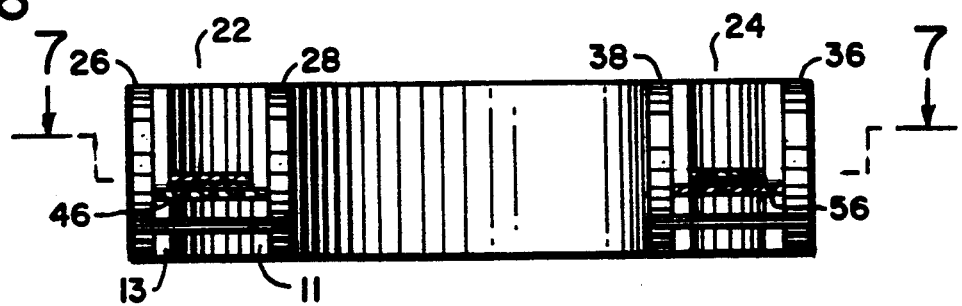
Figure 7:
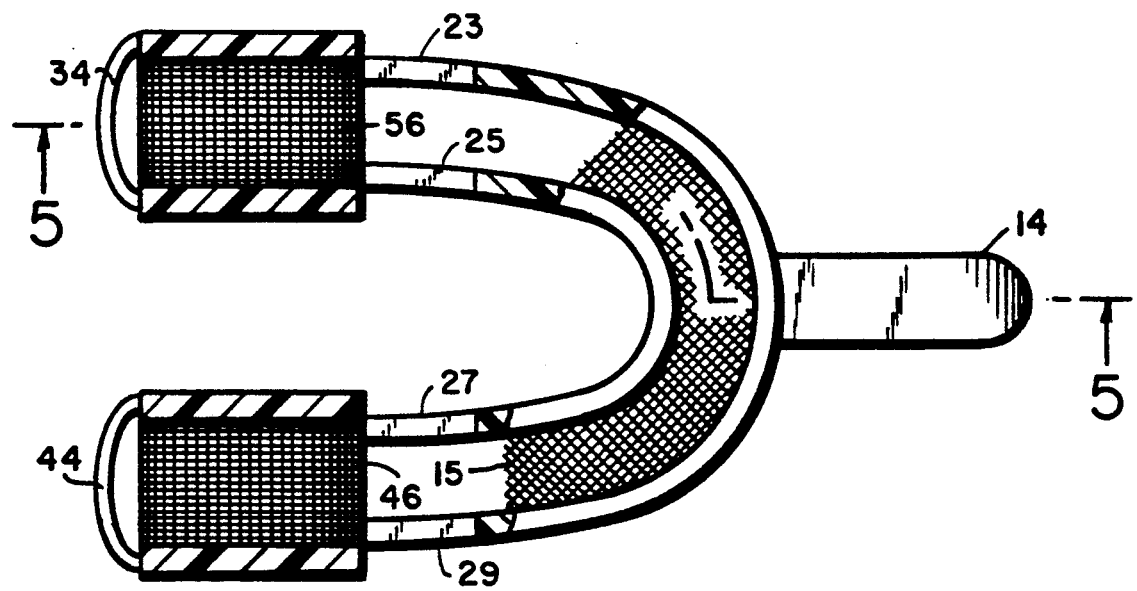
FIG. 7 is a top view partially in section along line 7—7 of FIG. 6.
Figure 8:
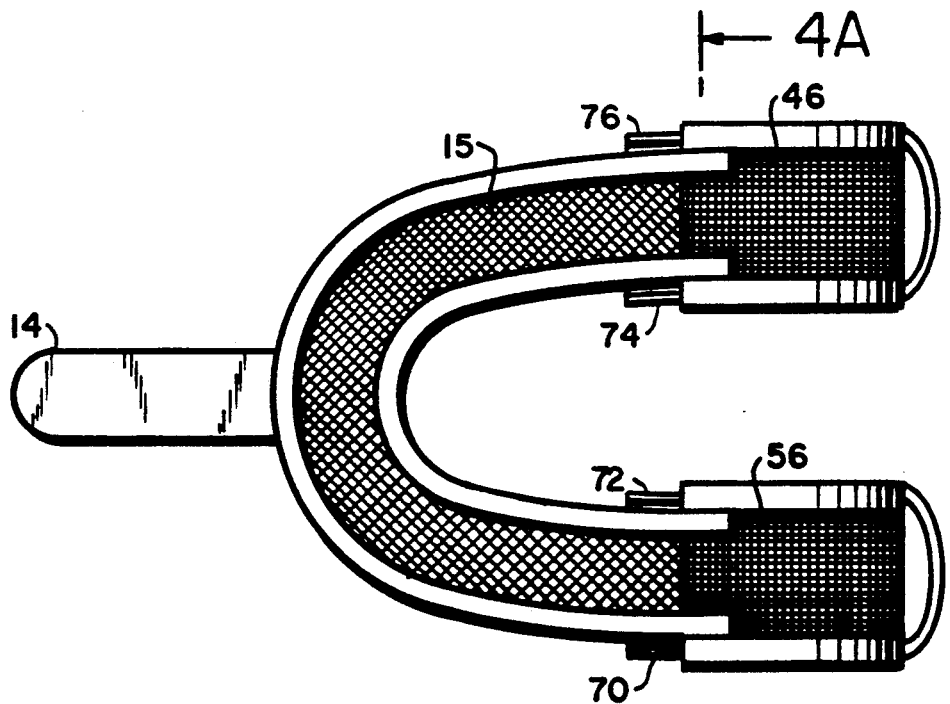
FIG. 8 is bottom plan view of the tray of FIG. 2.
Figure 9:
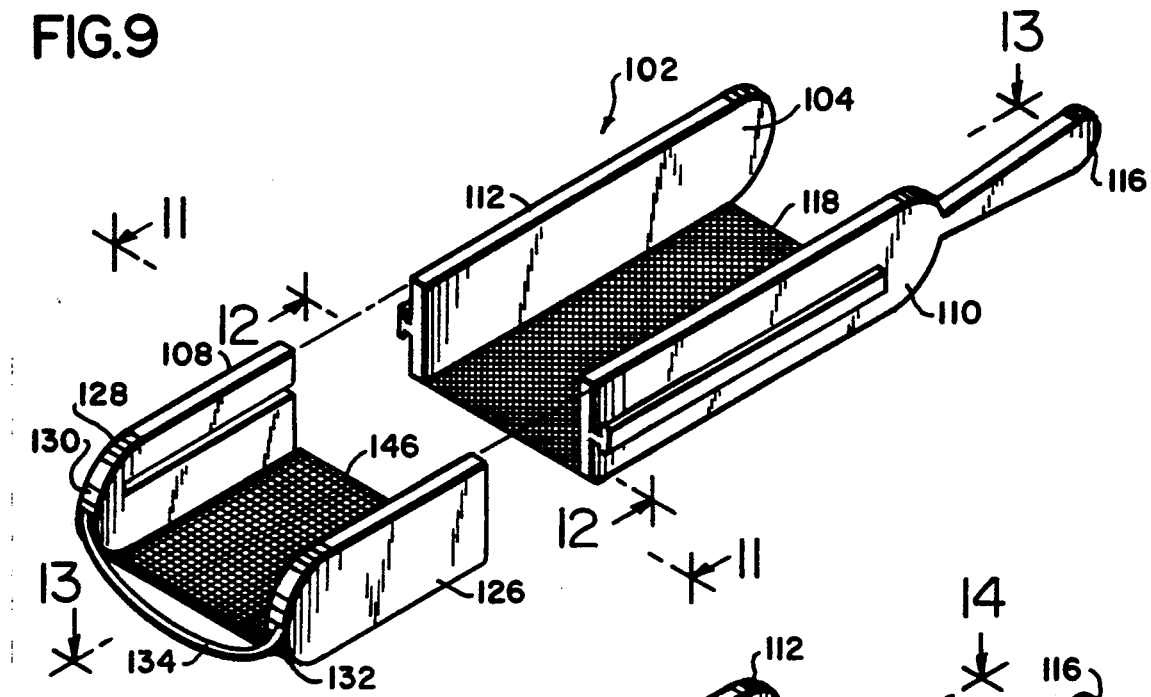
FIG. 9 is a perspective view of a quadrant impression tray with the parts shown separately.
Figure 10:
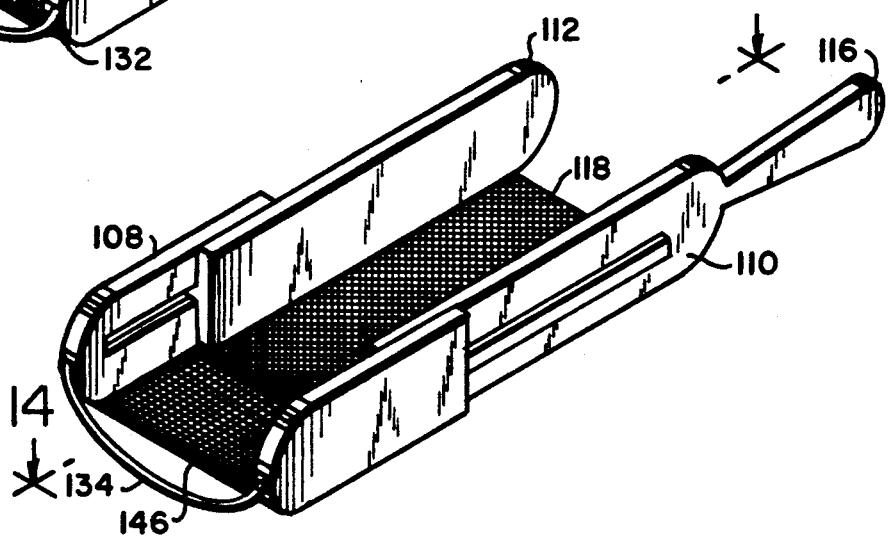
FIG. 10 is a perspective view of a quadrant impression with the sections together in overlapping relationship.
Figure 11:
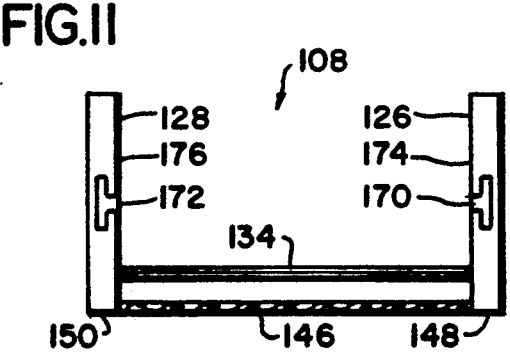
FIG. 11 is a sectional view along lines 11—11 of FIG. 9.
Figure 12:
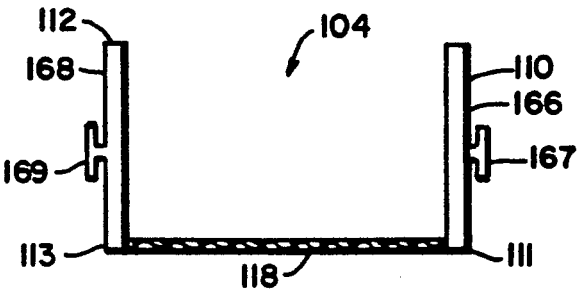
FIG. 12 is a elevational view along lines 12—12 of FIG. 9.
Figure 13:
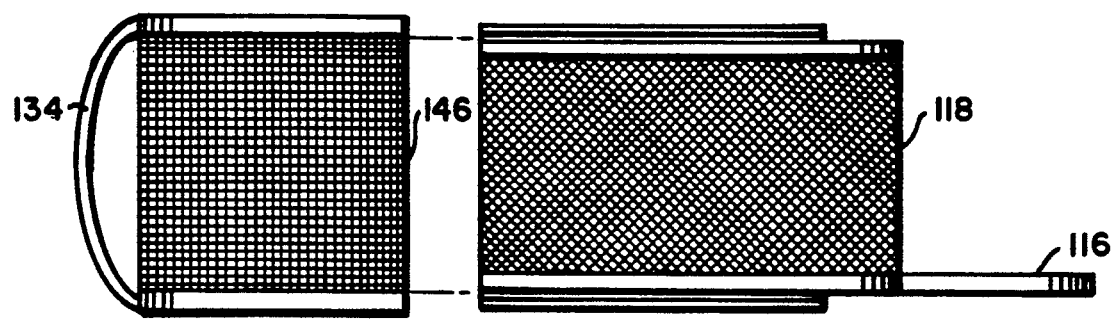
FIG. 13 is a top plan view of the tray as shown in FIG. 9.
Figure 14:
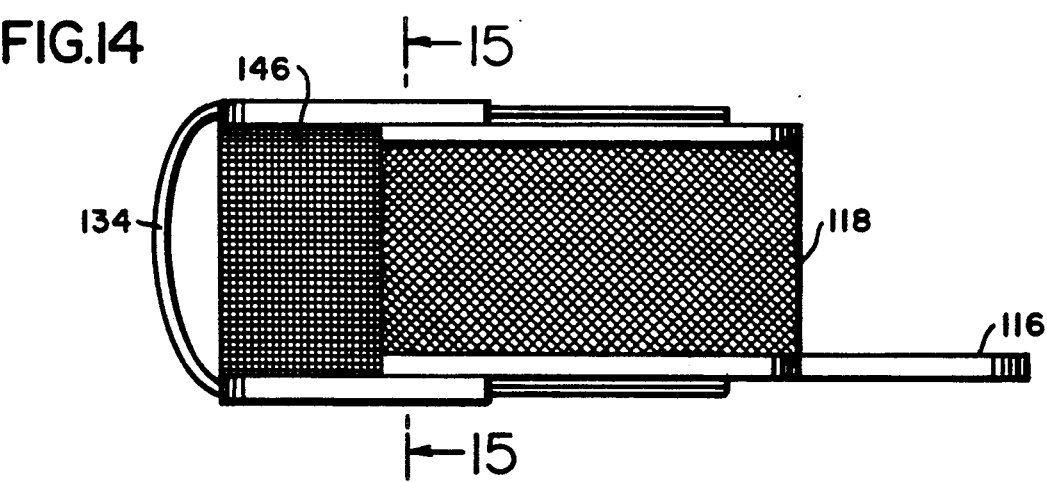
FIG. 14 is a top plan view of the tray as shown in FIG. 10.
Figure 15:
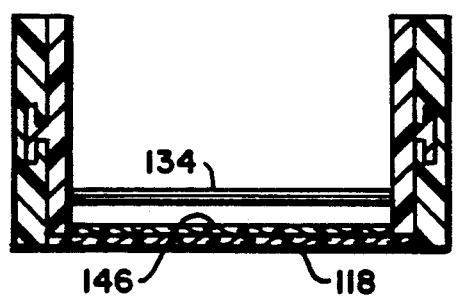
FIG. 15 is a sectional view along lines 15—15 of FIG. 13.

A fine flexible plastic woven mesh cloth such as Dacron mesh cloth 46 of a known type extends between the lower middle 48 of wall 26 and lower middle 50 of wall 28 of extension 22 as shown best in FIGS. 3, 5 and 6. It may be molded to the walls 26 and 28 respectively or adhesively secured thereto.

In a similar manner, cloth 56 extends between the middle 52 and 54 of walls 36 and 38 respectively of extension 24.

The middle 11 and 13 of walls 10 and 12 of the arcuate portion 8 are joined together by the mesh cloth 15.

The walls 10 and 12 on each branch 18 and 20 have horizontal slots 23, 25, 27, and 29 opening at the end 19 and 21 of each branch. The slots 23, 25, 27, and 29 are formed just below the mesh 15 and extend forward in the walls 10 and 12 a distance about equal to the length of the meshes 46 and 56 of the extension 22 and 24. This allows the mesh 46 and 56 to slide just under mesh 15 as the portion 8 and extension 22 and 24 are adjusted with respect to each other. Since the meshes 46 and 56 are located slightly higher the walls 26 and 28, and 36 and 38 that mesh 15 is on the walls 10 and 12.

The distances between the inner face 58 of wall 28 and inner face 60 of wall 26 of extension 22 and the distance between the inner face 62 of wall 36 and inner face 64 of wall 38 of extension 24 is only slightly more than the distance between the outer faces 66 and 68 of walls 10 and 12 respectively of portion 8.

This allows the extensions 22 and 24 to slide forward or backward o arcuate portion 8 to adjust for the conditions and size of an individual patient's mouth.

The outer faces 66 and 68 of wall 10 and wall 12 respectively towards the ends 19 and 21 and provided with rails 70, 72, 74, and 76 of T shaped cross section extending from the ends 19 and 21 forward a distance approximately equal to the length of the extension 22 and 24. The rails are preferably located approximately midway between the top and bottom of the walls 10 and 12. Corresponding recesses 80, 82, 84 and 86 of T shaped cross section are formed in the inner faces 58, 60, 62, and 64 respectively of walls 26, 28, 30, and 32 of the extension 22 and 24. The rails and recesses cooperate to hold the extension 22 and 24 adjustably together with arcuate portion 8.

In Figs. 9-15, an embodiment of the invention for quadrant impressions is shown, in this case for upper teeth only.

In this embodiment, a quadrant impression tray 102 has an anterior portion 104 which includes spaced apart inner wall 110 and outer wall 112. The tray has an extension portion 108 as shown. The anterior end 114 of the inner wall 110 has a handle 116 formed thereon. A woven plastic mesh 118 joins the bases 111 and 113 of the walls 110 and 112.

The extension portion 108 is similar to the extensions 22 and 24 of the preceding embodiment and includes spaced apart walls 126 and 128 joined at their posterior ends 130 and 132 respectively by the transverse member 134. A mesh cloth 146 extends between the base 148 of wall 126 and the base 150 of wall 128.

The walls 126 and 128 of extension 108 are slightly greater in height than the walls 110 and 112 of portion 104.

The outer surfaces 166 and 168 of walls 110 and 112 are provided with rails 167 and 169 respectively of T shaped cross section as in the first embodiment which ride in recesses 170 and 172 on corresponding cross sections formed in the inner faces 174 and 176 of the walls 110 and 112 respectively.

While this embodiment illustrates a tray for upper teeth, it is understood that it may be modified to extend the walls downward and provide slot in the walls 110 and 112 to accommodate mesh 146 in a manner similar to the first embodiment.

Figure 16:
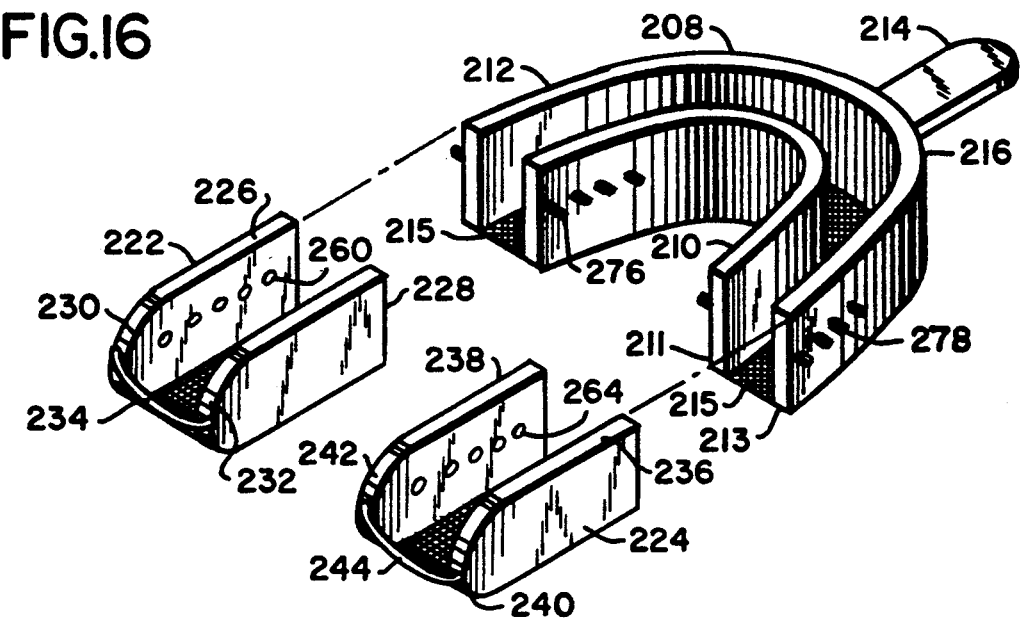
FIG. 16 is a perspective view of an alternative embodiment of the anterior impression tray wherein the extensions are held adjustably in place by nubs and recesses on the coacting parts, with the parts shown separately.
Figure 17:
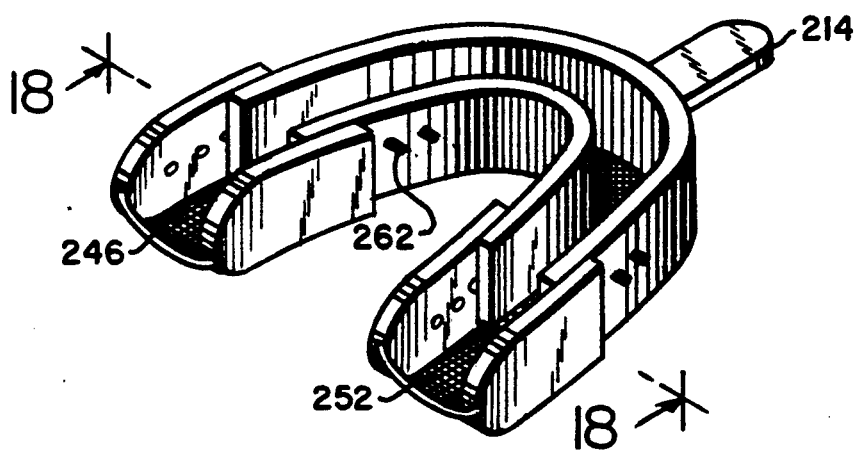
FIG. 17 is a perspective view of the embodiment of FIG. 16 with the parts assembled.
Figure 18:
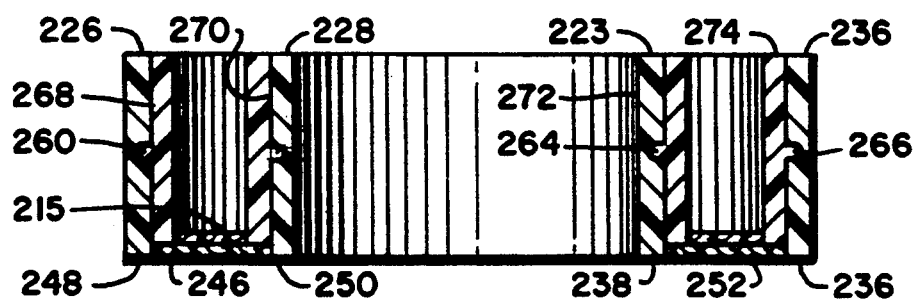
FIG. 18 is a sectional view along lines 18—18 of FIG. 17.

A further embodiment of the invention of the present application is shown in FIGS. 16–18 showing a different means for securing the parts in adjustable portions. In this case, an anterior impression tray 202 having a main arcuate portion 208 and spaced apart vertical walls 210 and 212 is shown with a handle 214 at the forward end 216. The walls 210 and 212 are joined at their bases 211 and 213 by mesh cloth 215 as the tray in the preceding embodiment.

Extension 222 has spaced apart vertical outer wall 226 and inner wall 228 joined at their posterior ends 230 and 232 respectively by the transverse member 234 which holds the walls 226 and 228 spaced apart and generally parallel to each other.

Similarly, extension 224 has spaced apart vertical outer wall 236 and inner wall 238 joined at their posterior ends 240 and 242 respectively by the transverse member 244.

The mesh cloth 246 extends between the base 248 of wall 226 and base 250 of wall 228 of the extension 222.

Similarly, cloth 252 extends between the bases 252 and 254 of walls 236 and 238 respectively of extension 224.

The walls 226 and 228 of extension 22 and the walls 236 and 236 of extension 224 are slightly greater in height than the walls 10 and 12 of the arcuate portion 8 so that the mesh 246 and 252 of extensions 222 and 224 passes below the cloth 215 and the bases and 213 of walls 210 and 212.

The parts are all flexible and dimensioned in a manner the same as those in the first embodiment.

In the present embodiment the arcuate portion 208 and the extensions 222 and 224 held together adjustably through the means of the cooperation of annular recesses 260, 262, 264, and 266 in the inner faces 268, 270, 272, and 274 of walls 226, 228, 236, and 238 of extensions 222 and 224 respectively, with corresponding annular nibs 276 and 278 on the outer surfaces of walls 210 and 212 respectively in place of the T shaped rails and recesses of the first embodiment.

In this present embodiment, the extensions as 212 and 224 are slid onto the rearward end 218 and 220 of portion 208 positioned thereon according to the configuration of the patient's mouth. The walls of the extensions 222 and 224 are flexible enough to spread outwardly for the wall of portion 8 as they are positioned over ends 218 and 220. When the extensions 222 and 224 are position, the walls thereof are released and the nits pushed into the recesses to lock the portion 208 and extension 222 and 224 into the desired position. The locking means of this embodiment may be utilized in the other embodiments.

In using each embodiment, once the tray is adjusted to the size of the patient's mouth the impression compound is placed on the mesh of the complete tray and the impression taken in usual manner.

The present invention provides a convenient and economical means of easily and rapidly taking dental impressions without the necessity of multiple sized non adjustable trays to stock or the inconvenience of adjusting unwieldy supposedly adjustable trays presently available.

While the invention has been described by reference to an illustrative embodiment, it is not intended that the novel device be limited thereby, but that modifications thereof are intended to be included as falling within the broad spirit and scope of the foregoing disclosure, the following claims and the appended drawings.

What is claimed is:

1. An adjustable dual dental impression tray comprising an anterior section having a pair of spaced apart vertical walls joined by a mesh cloth extending horizontally therebetween, left and right branches of said anterior section extending rearwardly, left and right posterior extension sections each comprising spaced apart vertical inner and outer walls joined by mesh cloth extending horizontally between inner surfaces of said inner and outer wall of said posterior sections, and securing means securing said posterior extension sections to said anterior section in sliding connection with said anterior section, and wherein said mesh of said anterior section extends between said walls at the approximate mid height of said walls, horizontal slots extending through said walls forwardly from the rear ends and located slightly below said mesh cloth of said anterior section to permit the mesh of said posterior extensions to move forward to overlap the mesh of said anterior section.

2. A tray as claimed in claim 1 wherein said securing means comprises horizontal T-shaped extensions extending from the outer surfaces of the rearward section of the rearwardly extending walls of said anterior section cooperating with horizontal recesses of T-shaped crossection in the exterior surfaces of the walls of said extension sections.

3. A tray as claimed in claim 1 wherein said securing means comprise cooperating annular nibs and recesses on the walls of said anterior section and extension sections.

4. An adjustable dual dental impression tray comprising an anterior section having spaced apart vertical walls joined by a mesh cloth extending horizontally therebetween, a posterior extension section comprising spaced apart walls having a mesh cloth extending therebetween, joining means at the posterior ends of said extension walls of said extension to hold said walls flexibly in place with respect to each other, slots formed n the walls of said anterior section and opening in the rear ends of said walls to allow the mesh of said extension to overlap the mesh of said anterior section a said extension is moved forward or rearward with respect to said anterior section, and securing means securing said extension section to said anterior section in sliding connection with said anterior section.

5. A tray as claimed in claim 4 wherein said securing means comprise cooperating annular nibs and recesses on the walls of said anterior section and extension section.

6. A tray as claimed in claim 4 wherein said securing means comprises horizontal T-shaped extensions extending from the outer surfaces of the rearward section of the rearwardly extending walls of said anterior section cooperating with horizontal recesses of T-shaped crossection in the exterior surfaces of the walls of said posterior extension section.

* * * * *